United States Patent [19]
Priegnitz

[11] 3,992,471
[45] Nov. 16, 1976

[54] PROCESS FOR THE SEPARATION OF 1,3-BUTADIENE BY SELECTIVE ADSORPTION ON A ZEOLITE ADSORBENT

[75] Inventor: James William Priegnitz, Elgin, Ill.

[73] Assignee: UOP Inc., Des Plaines, Ill.

[22] Filed: Oct. 9, 1975

[21] Appl. No.: 621,196

Related U.S. Application Data

[63] Continuation-in-part of Ser. No. 496,793, Aug. 12, 1974, abandoned.

[52] U.S. Cl. .................................... 260/681.5 R
[51] Int. Cl.² ..................................... C07C 7/00
[58] Field of Search ............... 260/68.15, 676 MS; 208/DIG. 2

[56] References Cited
UNITED STATES PATENTS

| | | | |
|---|---|---|---|
| 2,882,243 | 4/1959 | Milton | 260/676 MS |
| 3,106,593 | 10/1963 | Beuesi et al. | 260/681.5 R |
| 3,130,006 | 4/1964 | Rabo et al. | 208/DIG. 2 |
| 3,311,671 | 3/1967 | Baker | 260/681.5 R |
| 3,539,502 | 11/1970 | Griswold | 260/676 MS |
| 3,825,490 | 7/1974 | Vachnda | 260/683.65 |

Primary Examiner—Veronica O'Keefe
Attorney, Agent, or Firm—James R. Hoatson, Jr.; Thomas K. McBride; William H. Page, II

[57] ABSTRACT

A process for the separation of 1,3-butadiene from a feed mixture comprising 1,3-butadiene and at least one other $C_4$ unsaturate. A feed stream containing 1,3-butadiene and at least one other $C_4$ unsaturate is contacted at adsorption conditions including the liquid phase with an adsorbent comprising type X zeolite containing sodium or potassium cations at the exchangeable cationic sites to effect the selective adsorption of 1,3-butadiene. The adsorbent is then contacted with a desorbent material at desorption conditions including the liquid phase to effect the removal of 1,3-butadiene from the adsorbent. The 1,3-butadiene is thereafter separated by separation means from desorbent material and recovered as a purified product.

15 Claims, No Drawings

PROCESS FOR THE SEPARATION OF 1,3-BUTADIENE BY SELECTIVE ADSORPTION ON A ZEOLITE ADSORBENT

CROSS-REFERENCE TO RELATED APPLICATIONS

This application is a continuation-in-part application of my prior copending application Ser. No. 496,793 filed on Aug. 12, 1974, now abandoned, all the teachings of which are incorporated herein by specific reference thereto.

BACKGROUND OF THE INVENTION

1. Field of the Invention

In the field of art to which the claimed invention pertains is solid-bed adsorptive separation. More specifically, the claimed invention relates to a process for the separation of 1,3-butadiene from a feed mixture comprising 1,3-butadiene and at least one other $C_4$ unsaturate which process employs a solid adsorbent which selectively removes 1,3-butadiene from the feed mixture.

2. Description of the Prior Art

It is well known in the separation art that certain crystalline aluminosilicates can be used to separate hydrocarbons species from mixtures thereof. In particular, the separation of normal paraffins from branched chained paraffins can be accomplished by using the type A zeolites which have pore openings from 3 to 5 Angstroms. Such a separation process is disclosed for example in U.S. Pat. Nos. 2,985,589 and 3,201,491. These adsorbents allow a separation based on the physical size differences in the molecules by allowing the smaller or normal hydrocarbons to be passed into the cavities within the crystalline aluminosilicate adsorbent, while excluding the larger or branched chain molecules.

U.S. Pat. Nos. 3,265,750 and 3,510,423, for example, disclose processes in which larger pore diameter zeolites such as the type X or type Y structured zeolites can be used to separate olefinic hydrocarbons.

In addition to separating hydrocarbon types, the type X or type Y zeolite have also been employed in processes to separate individual hydrocarbon isomers. In the process described in U.S. Pat. Nos. 3,668,730, 3,668,732, 3,626,020, and 3,686,342, for example, they are used to separate desired xylene isomers; in U.S. Pat. No. 3,668,267 they are used to separate particular alkyl substituted naphthalenes.

The present invention relates to a process for the separation of 1,3-butadiene from a feed mixture comprising 1,3-butadiene and at least one other $C_4$ unsaturate with a particular zeolitic adsorbent.

I have found that adsorbents comprising type X or type Y zeolites, which have been found to work equally well in many other adsorptive processes, are not equivalent for use in this process. I have found that adsorbents comprising type X zeolites containing sodium or potassium at the exchangeable cationic sites possess both good adsorptive capacity and selectivity for 1,3-butadiene as well as low polymerization activity for 1,3-butadiene and are therefore suitable for use in my process. Furthermore the polymerization activity of the adsorbent can be further reduced by employing a particular adsorbent preparation procedure. In a preferred embodiment my process employs the adsorbent so produced in combination with operating conditions which include the liquid phase and a rather low temperature range of from about 25° to about 75° C. to minimize the polymerization of 1,3-butadiene and prolong the useful life of the adsorbent.

SUMMARY OF THE INVENTION

It is, accordingly, a broad objective of my invention to provide a process for the separation of 1,3-butadiene from a feed mixture comprising 1,3-butadiene and at least one other $C_4$ unsaturate by employing an adsorbent comprising a specific zeolite to selectively adsorb 1,3-butadiene from the feed mixture. It is another more specific objective of my invention to provide a process for separating 1,3-butadiene with a zeolitic adsorbent in which process polymerization of 1,3-butadiene is minimized thereby extending the useful life of the adsorbent used in the process.

In brief summary, my invention is, in one embodiment a process for separating 1,3-butadiene from a feed mixture comprising 1,3-butadiene and at least one $C_4$ mono-olefin which process comprises the steps of: (a) contacting said mixture at adsorption conditions including the liquid phase with an adsorbent comprising type X zeolite containing potassium or sodium cations at the exchangeable cationic sites thereby selectively adsorbing 1,3-butadiene; (b) withdrawing from the adsorbent a raffinate stream comprising a less selectively adsorbed $C_4$ mono-olefin; (c) contacting the adsorbent at desorption conditions which include the liquid phase with a desorbent material comprising an aromatic hydrocarbon to effect the removal of 1,3-butadiene from the adsorbent; (d) withdrawing from the adsorbent an extract stream comprising desorbent material and 1,3-butadiene and passing said extract stream to a separation means; and (e) separating in said separation means, maintained at separating conditions, said desorbent material from 1,3-butadiene.

In another embodiment my invention is a process for separating 1,3-butadiene from a feed mixture comprising 1,3-butadiene and at least one $C_4$ mono-olefin which comprises the steps of: (a) contacting said mixtures at adsorption conditions including the liquid phase with an adsorbent prepared by the steps of: (i) contacting a base material comprising a type X zeolite having a $Na_2O/Al_2O_3$ ratio less than about 0.7 with an aqueous sodium hydroxide solution at first ion exchange conditions to increase the sodium cation content to a $Na_2O/Al_2O_3$ ratio of greater than about 0.7; (ii) contacting the sodium-exchanged base material with an aqueous potassium salt solution at second ion exchange conditions to effect the essentially complete exchange of sodium cations with potassium cations; (iii) washing the material with water maintained at pH greater than 7 to remove excess potassium salt solution; and (iv) drying the material at drying conditions to reduce the LOI at 600° C. to less than about 10 wt. %, thereby selectively adsorbing 1,3-butadiene; (b) withdrawing from the adsorbent a raffinate stream comprising a less selectively adsorbed $C_4$ mono-olefin; (c) contacting the adsorbent at desorption conditions which include the liquid phase with a desorbent material comprising benzene or toluene to effect the removal of 1,3-butadiene from the adsorbent; (d) withdrawing from the adsorbent an extract stream comprising 1,3-butadiene and desorbent material and passing said extract stream to a fractionation means; and, (e) fractionating in said fractionation means maintained at fractionation conditions desorbent material from 1,3-butadiene.

Other embodiments and objects of the present invention encompass details about feed mixtures, adsorbents, desorbents, and operating conditions all of which are hereinafter disclosed in the following discussion of each of these facets of the present invention.

The process of this invention provides a superior alternative to such methods of concentrating or separating 1,3-butadiene as: extractive distillation with selective solvents; selective adsorption with cuprous salt solutions; azeotropic distillation with ammonia; and, sulfone formation. Of these methods, only the first two have achieved commercial prominence.

Butadiene, industrially the most important diolefin, is used to produce polymer components used, for example, in synthetic rubber and is also used as a chemical intermediate for a great variety of compounds.

DESCRIPTION OF THE INVENTION

Butadiene is synthesized commercially by four main methods: (1) by catalytic dehydrogenation of concentrated n-butylenes; (2) by catalytic dehydrogenation of n-butane; (3) as a by-product, in rather low yield, from severe high-temperature cracking of liquid hydrocarbons for production of unsaturates; and (4) from ethyl alcohol by a combination of catalytic dehydrogenation and dehydration. The first two methods are the most frequently used methods.

All of the conversion processes yield products in which 1,3-butadiene is mixed with other closely boiling hydrocarbons. For example, when concentrated 2-butene and 1-butene are catalytically dehydrogenated to produce 1,3-butadiene the stabilized effluent from this operation contains, in addition to 1,3-butadiene, unreacted isomeric n-butenes, some n-butane, isobutane, isobutylene, appreciable concentration of $C_3$ components, and small concentrations of components heavier than $C_4$ hydrocarbons.

Table 1 below lists the hydrocarbons frequently found in crude butadiene fractions from such sources. The relative amounts of these hydrocarbons present in crude butadiene vary considerably, depending upon the type of hydrocarbon conversion process employed. Other $C_4$ unsaturates, primarily mono-olefins, are always present in major amounts. Non-conjugated diolefins and acetylenes are minor constituents, but they generally increase with increasing temperature during hydrocarbon conversion. For the most part, however, they are highly objectionable contaminants in purified butadiene and hence their concentrations in the latter must be carefully controlled.

Ordinarily fractionation alone is incapable of separating 1,3-butadiene of the desired purity (ordinarily 98 wt. % or higher) from these mixtures. Commercially butadiene is separated from olefins and paraffins primarily by extractive distillation with selective solvents and by selective adsorption with cuprous salt solutions.

A polar solvent is employed in extractive distillation processes to increase the volatility of some components in the mixture relative to other components in the mixture with the result that separation of the desired component by distillation is made possible. Polar solvents such as acetonitrile, acetone, furfural, dimethylformamide, dioxane, phenol, and N-methylpyrrolidone, and their corresponding aqueous admixtures have been used in extractive distillation processes for 1,3-butadiene separation.

TABLE 1

COMPOUNDS IN A TYPICAL CRUDE BUTADIENE FRACTIONS AND THEIR NORMAL BOILING POINTS

| Compound | B.p., °C. |
| --- | --- |
| Paraffins: | |
| Propane | −42.1 |
| Isobutane | −11.72 |
| n-Butane | − 0.55 |
| Mono-olefins: | |
| Propylene (propene) | −47.6 |
| Isobutylene (methylpropene) | − 6.93 |
| 1-Butene | − 6.32 |
| trans-2-butene | 0.86 |
| cis-2-butene | 3.64 |
| 3-Methyl-1-butene | 18.8 |
| Diolefins: | |
| Propadiene (allene) | −34.3 |
| 1,3-Butadiene | − 4.54 |
| 1,2-Butadiene | 10.3 |
| 1,4-Pentadiene | 26.12 |
| Acetylenes: | |
| Methylacetylene | −23.2 |
| Vinylacetylene | 5.0 |
| Ethylacetylene | 8.6 |
| Butadiyne (biacetylene) | 10.3 |
| Dimethylacetylene | 27.1 |

In the conventional extractive distillation processes, the butanes and butenes exhibit an enhanced volatility relative to the diolefinic and acetylenic materials and are recovered as an overhead product from the extractive distillation zone. The less volatile hydrocarbons, e.g., the diolefins and higher acetylenes, are separated together with the polar solvent as the bottoms product from the extractive distillation zone. The butadiene product is recovered directly from the bottoms product in a stripping zone at elevated temperature. The energy required to effect the separation in the extractive distillation zone and in the stripping zone is supplied by reboilers attached to each zone.

The extractive distillation method suffers from several disadvantages. One disadvantage is that relatively large amounts of energy are required to reboil both the extractive distillation zone, which is typically a 100 plate column, and the stripping zone. Another disadvantage is that solvent losses occur in several ways during extractive distillation. Physical losses occur from leakage and from carryover in the raffinate. Other losses occur from chemical reactivity or thermal degradation of the solvent. In the case of phenol for instance, a high boiling inactive sludge forms from reaction with traces of dienes present in the hydrocarbon feed. Furfural is sensitive to elevated temperatures in the presence of oxygen, water, or unsaturated hydrocarbons resulting in polymerization. Thus, continuous redistillation of a portion of the circulating solvent or intermittent redistillation of the total solvent inventory is usually required to remove such solvent impurities. Additionally, control of the extractive distillation is usually difficult. The temperature gradient in the tower does not correlate with the actual separation being carried out. Control is usually by material balance supplemented by frequent product samples and analyses and in some cases spectroscopic or chromatographic instruments have been employed for continuous analysis to aid in tower operation.

Selective absorption with cuprous salt solutions is also commercially used to purify butadiene from crude fractions derived from both thermal cracking and catalytic dehydrogenation processes. The solubility of a hydrogen in solutions of this type generally increases with the degree of unsaturated, butadiene being many times more soluble than the closely-boiling butenes. Essentially three processing steps are involved in this purification operation; an absorption stage in which butadiene, along with a portion of the mono-olefins and other unsaturates, is dissolved in the solvent; an enrichment stage, generally effected by a combination of heating and stripping with enriched butadiene, in which essentially all of the dissolved hydrocarbons except butadiene are stripped from the solvent; and a desorption stage in which purified butadiene is stripped from the enriched solvent. By appropriate recycling of steams between these stages, high recoveries of butadiene can be obtained. Like extractive distillation, however, this process also has rather high energy requirements and has the same attendant problems of circulating-solvent life and contamination or degradation.

The process of my invention avoids the problems associated with reactive circulating solvents and provides a process less difficult in operation by which high purity butadiene can be produced at operating costs competitive with those of existing processes.

To separate 1,3-butadiene from a feed mixture containing 1,3-butadiene and at least one other $C_4$ unsaturate by the process of my invention, the mixture is contacted with a particular adsorbent and the butadiene is more selectively adsorbed and retained by the adsorbent while the less selectively adsorbed other $C_4$ unsaturate is removed from the interstitial void spaces between the particles of adsorbent and the surface of the adsorbent. The adsorbent containing the more selectively adsorbed 1,3-butadiene is referred as a "rich" adsorbent — rich in the more selectively adsorbed 1,3-butadiene.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. As previously mentioned, the crude butadiene feed mixtures will usually contain many components — primarily $C_3$'s and $C_4$'s — and it will therefore be recognized that all of the components present in the feed mixture, other than 1,3-butadiene, will be less selectively adsorbed by the adsorbent with respect to 1,3-butadiene. Thus, the raffinate stream will contain as raffinate components all of the feed components besides 1,3-butadiene and the extract stream will contain 1,3-butadiene as the extract component.

Although it is possible by the process of this invention to produce high purity (98% or greater), 1,3-butadiene at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed 1,3-butadiene to the concentration of less selectively adsorbed butene-1 will be highest in the extract stream, next highest in the feed mixture, and lowest in the raffinate stream. Likewise, the ratio of the less selectively adsorbed butene-1 to the more selectively adsorbed 1,3-butadiene will be highest in the raffinate stream, next highest in the feed mixture, and the lowest in the extract stream.

The adsorbent can be contained in one or more chambers where through programmed flow into and out of the chambers separation of 1,3-butadiene is effected. The adsorbent will then be contacted with a desorbent material which is capable of displacing the adsorbed 1,3-butadiene from the adsorbent. The adsorbent may be employed in the form of a dense compact fixed bed which is alternatively contacted with the feed mixture and a desorbent material (hereinafter described). In the simplest embodiment of the invention the adsorbent is employed in the form of a single static bed in which case the process is only semi-continuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the adsorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving bed processes the adsorption and desorption operations are continuously taking place which allows both continuous production of an extract and a raffinate stream and the continual use of feed and desorbent streams. One preferred processing flow scheme which can be utilized to effect the process of this invention includes what is known in the art as the simulated moving-bed countercurrent flow system. The operating principles and sequence of such a flow system are described in U.S. Pat. No. 2,985,589 issued to D. B. Broughton. In such a system it is the progressive movement of multiple liquid access points down an adsorbent chamber that simulates the upward movement of adsorbent contained in the chamber. Only four of the access lines are active at any one time; the feed input stream, desorbent input stream, raffinate output stream, and the extract output stream access lines. Coincident with this simulated upward movement of the solid adsorbent is the movement of the liquid occupying the void volume of the packed bed of adsorbent. So that countercurrent contact is maintained, a liquid flow down the adsorbent chamber is provided by a pump. As an active liquid access point moves through a cycle, that is, from the top of the chamber to the bottom, the chamber circulation pump moves through different zones which require different flow rates. A programed flow controller may be provided to set and regulate these flow rates.

The active liquid access points effectively divided the adsorbent chamber into separate zones, each of which has a different function. Zone 1, bounded by the feed input stream and raffinate output stream access points, is the adsorption zone. The adsorbent entering this zone at the raffinate out access point contains only the raffinate components and desorbent. As it rises and contacts the descending liquid which is richer in the extract components, the selectivity of the adsorbent for the extract components causes them to be adsorbed.

The displaced desorbent and raffinate components are withdrawn as the raffinate output stream. The adsorbent leaving the zone at the feed in excess point contains all of the adsorbed species. Zone 2, bounded by the feed input stream and extract output stream access points, is the purification zone. The descending liquid entering this zone, being rich in extract components and desorbent, causes the replacement of the raffinate components from the ascending adsorbent. Zone 3, bounded by the extract output stream and desorbent input stream access points, is the desorption zone. The rising adsorbent from Zone 2, containing extract components and desorbent, is contacted by the descending desorbent stream, resulting in the desorption of the extract components. The exiting extract output stream contains both desorbent and extract components. Optional Zone 4, a buffer zone, is bounded by the raffinate output stream and desorbent input stream access points. Here, desorbent from the ascending adsorbent is desorbed by the raffinate components in the liquid from Zone 1. The desorbent reclaimed reduces the quantity of external desorbent required to desorb the extract components in Zone 3. Separation means, typically fractionators, are used to separate the extract and raffinate components from the desorbent in the extract output and raffinate output streams. In one embodiment our process will employ this simulated moving bed countercurrent flow system just described.

Adsorption and desorption conditions for most adsorptive separation processes can generally be either in the liquid or vapor phase or both but for the process of this invention all liquid-phase operations are preferred because lower temperatures are required than for vapor phase operations. Low operating temperatures are preferred for this process to minimize the rate of 1,3-butadiene polymerization and thus directionally prolong the useful life of the adsorbent. Operating conditions will include temperatures within the range of from about 25° C. to about 100° C. with a preferred range being from about 25° C. to about 75° C. Operating pressure is not critical and need be only high enough to insure liquid phase operation. Operating pressure will be in the range of from about atmospheric to about 500 psig. Desorption conditions for this process will generally include the same range of temperatures and pressures as used for adsorption operations.

The term "desorbent material" as used herein generally means any substance capable of removing a selectively adsorbed feed component from the adsorbent. In adsorptive separation processes in which the selectively adsorbed feed component is removed from the adsorbent by a purge stream, desorbent materials such as methane, ethane, etc., or other types of gases such as nitrogen or hydrogen may be used at elevated temperatures or reduced pressure or both to effectively purge the adsorbed feed component from the adsorbent.

However, in processes in which are generally operated at substantially constant pressures and temperatures to insure liquid phase, the desorbent material relied upon must be judiciously selected in order that it may displace the adsorbed feed component from the adsorbent with reasonable mass flow rates and also without unduly preventing the extract component from displacing the desorbent in a following adsorption cycle. Desorbent materials which can be used in the process of this invention should additionally be substances which are easily separable from the feed mixture that is passed into the process ince both the extract stream and the raffinate stream removed from the adsorbent contain desorbent material. Without a method of separating desorbent materials, the purity of the extract product and the raffinate product would not be very high since they would be diluted with desorbent. The extract stream and the raffinate stream are therefore directed to separation means, typically fractionators, for separation of the desorbent material. Thus it is contemplated that any desorbent material used in this process will have a different average boiling point than that of the feed mixture to permit separation therefrom by distillation and reuse of the desorbent material in the process. Preferably the difference between the average boiling points shall be at least about 20° F. The boiling range of the desorbent material could be higher or lower than that of the feed mixture.

I have found that desorbent materials comprising aromatics, particularly benzene and toluene, are particularly effective in this process. A desorbent material comprising benzene is suitable for use with an adsorbent containing either sodium-type X or potassium-type X zeolite while a desorbent material comprising toluene appears best suited to an adsorbent containing potassium-type X zeolite. I have found that mixtures of benzene or toluene in paraffins or naphthenes perform better as desorbent materials than do 100 vol. % benzene or toluene and are therefore preferred. At the 100 vol. % concentration level of benzene or toluene there is a tendency for 1,3-butadiene to "tail" during the desorption operation rather than desorb cleanly and quickly. The paraffins or naphthenes will have boiling points different from the feed to allow separation by distillation from feed components. Typical aromatic concentrations when used in admixtures with a paraffin or a naphthene can be from a few volume percent up to near 100 vol. % of the total desorbent material and preferably will be within the range of from about 25 vol. % to about 100 vol. % with an even more preferred range being from about 50 vol. % to about 100 vol. % of the total desorbent material.

With the types and some operating features of processes employing adsorbents to separate 1,3-butadiene by selective adsorption now in mind, one can appreciate that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; sufficiently fast rates of adsorption and desorption of the extract component to and from the adsorbent; and, little or no catalytic activity for undesired reactions such as polymerization and isomerization.

Capacity of the adsorbent for adsorbing a specific volume of an extract component, is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Selectivity can be expressed not only for one feed mixture component as compared to another but can also be expressed between any feed mixture component and the desorbent. The selectivity, (B), as used throughout this specification is defined as the ratio of the two components of the adsorbed phase over the ratio of the same two components in the unadsorbed phase at equilibrium conditions.

Selectivity is shown as Equation 1 below:

EQUATION 1

$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions as defined here were determined when the feed passing over a bed of adsorbent did not change composition after contacting the bed of adsorbent. In other words, there was no net transfer of material occurring between the unadsorbed and adsorbed phases.

As can be seen where the selectivity of two components approaches 1.0 there is no preferential adsorption of one component by the adsorbent. As the (B) becomes less than or greater than 1.0 there is a preferential selectivity by the adsorbent of one component. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Desorbents ideally would have a selectivity equal to about 1 or slightly less than 1.

The third important characteristic is the rate of exchange of the extract component of the feed mixture material or, in other words, the relative rate of desorption of the extract component. This characteristic relates to the amount of desorbent material that must be employed in the process to recover the extract component from the adsorbent; faster rates of exchange reduce the amount of desorbent material needed to remove the extract component.

It is also necessary that the adsorbent possess little or no catalytic activity toward polymerization or isomerization of any of the feed components. Such activity might effect adsorbent capacity or selectivity or product yields or all of these. Polymerization tends primarily to degrade the adsorbent in addition to reducing yields somewhat. Polymerization effects are generally considered to be primarily physical impediments which can prevent the adsorption of the extract component by obstructing the surface of the adsorbent and the pores present in the structure of the adsorbent. This shortens the useful life of the adsorbent and makes necessary frequent regeneration treatments to restore the adsorptive properties of the adsorbent. Isomerization activity tends primarily to decrease the yield of a desired feed component. It is the elimination of polymerization activity which we have found to be of primary concern rather than isomerization activity in the process of my invention. While reducing the temperature of the operations of the adsorption process in which the activity is present will help reduce the activity because of the associated reduction in the rate of reaction, a temperature reduction below some lower limit is not desirable because the reduction in temperature also reduces the rates of adsorption and desorption of the extract component. It is, therefore, extremely important that the catalytic activity be substantially reduced or preferably totally eliminated by proper methods of manufacture of a selected adsorbent.

In order to test various adsorbents to measure the characteristics of adsorptive capacity and selectivity, a dynamic testing apparatus is employed. The apparatus consists of an adsorbent chamber of approximately 70 cc. volume having inlet and outlet portion at opposite ends of the chamber. The chamber is contained within a temperature control means, and, in addition, pressure control equipment is used to operate the chamber at a constant predetermined pressure. Chromatographic analysis equipment can be attached to the outlet line of the chamber and used to analyze the effluent stream leaving the adsorbent chamber.

A pulse test, performed using this apparatus and the following general procedure, is used to determine selectivities and other data for various adsorbent systems. An adsorbent system comprises a particular adsorbent, feed material, and desorbent material. The adsorbent is filled to equilibrium with a particular desorbent material by passing the desorbent material through the adsorbent chamber. At a convenient time, a pulse of feed containing known concentrations of a non-adsorbed paraffinic tracer (n-butane for instance), 1,3-butadiene, and at least one other $C_4$ unsaturate all diluted in desorbent material is injected into the test chamber for a duration of several minutes. Desorbent flow is resumed, and the tracer and the other feed components are eluted as in a liquid-solid chromatographic operation. The effluent can be analyzed by on-stream chromatographic equipment and traces of the envelopes of corresponding feed component peaks developed. Alternatively, effluent samples can be collected periodically and later analyzed separately by gas chromatography.

From information derived from the chromatographic traces, adsorbent performance can be rated in terms of capacity index for an extract component, selectivity for one feed component with respect to the other (usually an extract component with respect to a raffinate component) and the rate of desorption of extract component by the desorbent. The capacity index may be characterized by the distance between the center of the peak envelope of the extract component and the peak envelope of the tracer component or some other known reference point. It is expressed in terms of the volume in cubic centimeters of desorbent pumped during this time interval. Selectivity, (B), for the extract component with respect to raffinate component is characterized by the ratio of the distance between the center of the extract component peak envelope and the tracer peak envelope (or other reference point) to the corresponding distance for the raffinate component. The rate of exchange of the extract component can generally be characterized by the width of the extract component peak envelope at half intensity. The narrower the peak width, the faster the desorption rate. The desorption rate can also be characterized by the distance between the center of the tracer peak envelope and the disappearance of the extract component which has just been desorbed. This distance is again the volume of desorbent pumped during this time interval.

In measuring the polymerization activity of the type X adsorbent, the same gas chromatographic equipment and testing apparatus was used. Two variations of a polymerization test can be used. In the first variation, the degree of polymerization activity may be measured by the loss of a known concentration of feed olefin or diolefin as detected in the effluent stream by the chromatographic equipment. The measure of polymerization is then an indirect determination being related to the difference between the inlet and outlet olefin or diolefin concentrations. Equation 2 below represents the formula used to determine catalytic activity of an adsorbent knowing the peak height of the olefin or diolefin remaining in the effluent stream leaving the adsorbent chamber and the peak height of the olefins present in the feed.

EQUATION 2

Adsorbent Activity = $100 - 100 \frac{(Pe)}{(Pf)}$ where Pe represents the peak height of the effluent olefins and Pf represents the peak height of the feed olefins. Thus an effluent peak height equal to one-half that of the feed would represent exactly 50% polymerization of the feed olefin component. The adsorbent polymerization activity would therefore by 50%.

The second variation of the catalytic activity test is to measure the polymer formed directly in the effluent stream with the chromatographic equipment. This method depends upon selecting a feed compound, such as diisobutylene, that easily forms an identifiable polymer. The dimer peak height above the base line is then used as the measure of polymerization and catalytic activity is reported as dimer units. The first variation is particularly useful to initially determine the catalytic activity of various adsorbents while the second variation is particularly useful in more accurately determining catalytic activity of adsorbents shown by the first test variation to have low catalytic activity.

To translate this type of adsorbent capacity, selectivity, and activity data into a practical separation process requires actual testing of the feed stream, desorbent material and adsorbent in a continuous countercurrent liquid-solid contacting device. The general operating principles of such a device has been previously described and are found in Broughton U.S. Pat. No. 2,985,589. A specific laboratory-size apparatus utilizing these principles is described in de Rosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are being withdrawn through two more. All remaining access lines are inactive and when the position of the distributing valve is advanced by one index, all active positions will be advanced by one bed. This simulates a condition in which the adsorbent physically moves in a direction countercurrent to the liquid flow. Additional details of the above-mentioned adsorbent testing apparatus and adsorbent evaluation techniques may be found in the paper "Separation of $C_8$ Aromatics by Adsorption" by A. J. de Rosset, R. W. Neuzil, D. J. Korous, and D. H. Rosback presented at the American Chemical Society, Los Angeles, California, Mar. 28 through Apr. 2, 1971.

The feasibility of separating 1,3-butadiene from a feed mixture comprising 1,3-butadiene and at least one other $C_4$ unsaturate by selective adsorption, which was demonstrated by pulse test results, was confirmed by continuous testing in the laboratory-sized apparatus described above.

Adsorbents used in the process of this invention will comprise specific crystalline aluminosilicates or molecular sieves and can comprise both the natural and synthetic aluminosilicates. particular crystalline aluminosilicates encompassed by the present invention include aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as molecular sieves when the separation which they effect is dependent essentially upon distinction between molecule sizes.

In the process of this invention, however, the term molecular sieves is not strictly suitable since the separation of 1,3-butadiene apparently takes place because of electrochemical attraction due to differences in the degree of unsaturation between 1,3-butadiene and other feed components rather than pure physical size differences in the molecules of the feed components.

In hydrated form, the crystalline aluminosilicate generally encompass those zeolites represented by the formula 1 below:

FORMULA 1

$M_{2/n}O:Al_2O_3:wSiO_2:yH_2O$ where "M" is a cation which balances the electrovalence of the tetrahedra and is generally referred to as an exchangeable cationic site, n represents the valence of the cation, w represents the moles of $SiO_2$, and y represents the moles of water. The generalized cation M may be one or more of a number of specific cations.

The prior art has generally recognized that adsorbents comprising the type X and the type Y zeolites can be used in certain adsorptive separation processes. These zeolites are described and defined in U.S. Pat. Nos. 2,882,244 and 3,120,007 respectively. The terms "type X" and "type Y" zeolites as used herein shall include all zeolites which have general structures as represented in the above two cited patents.

The type X zeolite in the hydrated or partially hydrated form can be represented in terms of mole oxides as shown in Formula 2 below:

FORMULA 2

$(0.9\pm0.2)M_{2/n}O:Al_2O_3:(2.5\pm0.5)SiO_2:yH_2O$ where M represents at least one cation having a valence of not more than 3, n represents the valence of M, and y is a value up to about 9 depending upon the identity of M and the degree of hydration of the crystal. As noted from Formula 2 the $SiO_2/Al_2O_3$ mole ratio for the type X zeolite is 2.5±0.5. The cation M may be one or more of a number of cations such as the hydrogen cation, the alkali metal cation, or the alkaline earth cations, or other selected cations, and is generally referred to as an exchangeable cationic site. As the type X zeolite is initially prepared, the cation M is usually predominately sodium and the zeolite is therefore referred to as a sodium-type X zeolite. Depending upon the purity of the reactants used to make the zeolite, other cations mentioned above may be present, however, as impurities.

The type Y zeolite in the hydrated or partially hydrated form can be similarly represented in terms of mole oxides as in Formula 3 below:

FORMULA 3

$(0.9\pm0.2)M_{2/n}O:Al_2O_3:wSiO_2:yH_2O$ where m is at least one cation having a valence not more than 3, n represents the valence of M, w is a value greater than about 3 up to 8, and y is a value up to about 9 depending upon the identity of M, and the degree of hydration of the crystal. The $SiO_2/Al_2O_3$ mole ratio for type Y zeolites can thus be from about 3 to about 8. Like the the type X zeolite, the cation M may be one or more of a variety of cations but, as the type Y zeolite is initially prepared, the cation M is usually predominately sodium with the other cations present usually as impurities. The type Y zeolite containing predominately sodium cations at the exchangeable cationic sites is therefore referred to as a sodium-type Y zeolite.

Adsorbents contemplated for use in this process will comprise only certain type X zeolites. Adsorbents comprising the type Y zeolites I have found have smaller retention volumes for 1,3-butadiene than adsorbents comprising type X zeolites and are therefore unsuitable for use in the process of my invention. Thus although the pore size of the type X or type Y zeolites are about the same, their suitability for separating 1,3-butadiene in my process is not the same. More specifically I have found that adsorbents comprising type X zeolites containing sodium or potassium cations at the exchangeable cationic sites possess the combination of characteristics or properties necessary for use in my process.

One of the adsorbent characteristics (all of which are hereinafter discussed in more detail) is that the adsorbent possess little or no catalytic activity toward polymerization or isomerization which would degrade the product quality, reduce the overall yield of desired product and shorten the useful life of the adsorbent. I have found that for the separation of 1,3-butadiene the polymerization effects of the adsorbent are of primary concern. Unless the adsorbent possesses little or no polymerization activity, 1,3-butadiene will rapidly polymerize to form a polymer which covers active adsorptive sites of the adsorbent thereby significantly shortening the useful life of the adsorbent making frequent shutdowns for adsorbent relacement or regeneration necessary. In one embodiment I have found that ion-exchanging a base material comprising sodium-type X zeolite with a dilute caustic solution followed by water washing and drying produces a finished adsorbent with little or no catalytic activity for polymerization. This step apparently eliminates non-sodium cations present at the exchangeable cation sites, such as hydrogen cations, which catalyze the polymerization reaction. The caustic solution may be sodium hydroxide or potassium hydroxide. Although an adsorbent comprising potassium-type X zeolite may be formed in a single step if dilute potassium hydroxide is used, it is preferred that the base material first be ion-exchanged with sodium hydroxide solution and then subsequently ion-exchanged with a potassium salt solution. The two-step procedure appears to produce a more inert potassium-type X zeolite.

The term "base material" as used herein shall refer to a type X zeolite-containing starting material used to make an adsorbent having particularly low polymerization activity. Generally the base material will be in the form of particles such as extrudates, aggregates, tablets, pills, macrospheres, or granules produced by grinding any of the above to a desired size range. The type X zeolite will usually be present in the base material in concentrations ranging from about 75 wt. % to about 98 wt. % of the base material based on a volatile free composition with the remaining material in the base material being amorphous material such as silica or alumina or both present in intimate mixture with the zeolite material. This amorphous material may be an adjunct of the manufacturing process of the zeolite (for example, intentionally incomplete purification of the zeolite during its manufacture) or it may be added to the relatively pure zeolite powder to aid in forming or agglomerating particles of the zeolite.

One example of a base material is commercially-available Linde Molecular Sieves 13X, a nominal 1/16-inch extrudate comprising 13X zeolite and a minor amount of amorphous material as binder. This base material is primarily in the sodium form; that is, the cation represented as M in formula 2 above is primarily sodium. By chemical analysis the $Na_2O/Al_2O_3$ ratio of this base material is usually about 0.7 or less can can typically be about 0.6. Other cations such as H+ and any of the Group IIA metal cations may be present, primarily as impurities, to supply the remainder of the cations needed for chemical balance and to meet the $0.9\pm0.2$ $Na_2O/Al_2O_3$ ratio. The silica to alumina ratio of this starting material by X-ray determination is about 2.5 and the same ratio by chemical analysis is about 2.6. Normally the base material, whether in the extrudate or pellet form, will be granulated to a particle size range of about 20–40 mesh (Standard U.S. Mesh) before the first ion-exchange step is begun. This is approximately the desired particle size of the finished adsorbent to be used in my process.

The caustic treatment step is primarily an ion-exchange step (and will be referred to as the first ion exchange) since the sodium cations present in the sodium hydroxide solution replace non-sodium impurities in the type X or type Y zeolite contained in the base material thereby converting the zeolite essentially completely to the sodium form. More specifically, to produce an acceptable adsorbent it is preferred that the sodium content of the starting material, as characterized by the weight ratio $Na_2O/Al_2O_3$ be increased to a ratio greater than about 0.70 and more preferably from about 0.75 to 1.0. First ion exchange conditions should be so regulated to achieve this degree of ion exchange.

Although mild ion-exchange conditions are employed for this first ion exchange, this step additionally removes a small amount of silica and alumina. Total silica and alumina removal from the base material is from about 1 to about 15% and is generally in the range of about 1 to 5 wt. %. Analyses indicate that the bulk of both soluble and insoluble material removed from the base material is aluminum as alumina or sodium aluminate. At least a portion of the alumina extracted appears to be from the zeolite itself rather than from any amorphous material since there is some nominal loss of zeolite as detected by X-ray analysis after this step. It is not known whether the small amount of silica removed from the base material came from the crystalline (zeolite) portion or the amorphous portion of the base material.

The degree of ion exchange and extraction of alumina achieved is a function of the three variables of caustic concentration, temperature at which the ion exchange is conducted, and the length of time the ion exchange is continued.

The sodium hydroxide used to prepare the aqueous sodium hydroxide solution should be of high purity having very low levels of both other Group IA impurities and Group IIA impurities. Suitable concentrations to obtain the desired ion exchange can be from about 0.5 to 10 wt. % of the sodium hydroxide with the preferred concentration being from about 0.5 to 5 wt. %. By using solutions containing sodium hydroxide within these ranges of concentration, the desired ion exchange can be obtained at temperatures from about 10° to about 120° C. with temperatures from about 65° to about 120° C. being especially preferred. Operating pressure is not critical and need only be sufficient to insure a liquid phase. Operating pressures can range from about atmospheric pressure to about 100 psig. The length of time required for the ion exchange will vary, depending upon the solution concentration and temperature, from about 0.5 to 5 hours. Within the above preferred concentrations and temperature ranges, a contact time which has been shown to be especially preferred is about 2 to 3 hours. Continuous or batch-type operations can be employed. The ion-exchange step should be controlled so that the zeolite structure will not be destroyed and so that the exchanged material will have a $Na_2O/Al_2O_3$ ratio greater than about 0.7 and more preferably from about 0.75 to 1.0. Periodic sampling and analyses can be employed to monitor the progress of this step.

After the ion-exchange step the ion-exchanged base material may be washed to remove excess sodium hydroxide solution and dried to a desired water content or it may be treated at second ion-exchange conditions to effect the essentially complete exchange of the sodium cations at the exchangeable cationic sites in the zeolite with potassium cations and then washed and dried. The potassium exchange will be performed by contacting the sodium-exchanged base material at second ion-exchange conditions with an aqueous solution of a soluble potassium salt to achieve the essentially complete exchange of sodium cations with potassium cations.

Second ion-exchange conditions will include a temperature of from about 10° C. to about 120° C. and a pH sufficient to preclude the formation of the hydrogen form of the zeolite. The pH will therefore be greater than 7 and preferably within the range of 7 to 10. Operating pressure is not critical and need only be sufficient to insure a liquid phase. Operating pressures can range from about atmospheric pressure to about 150 psig. The length of time for the essentially complete exchange of the sodium cations will be from about 0.5 to about 5 hours depending upon the concentration of the cation in the ion exchange medium and the temperature. The term "essentially complete exchange" as used herein shall mean that the sodium cation content of the base material has been reduced to about 2.0 wt. % or less and more preferably to about 1 wt. % or less.

The wash medium will be water which has a pH greater than 7 and preferably within the range of 7 to about 10. If necessary the water is adjusted to and maintained at the desired pH by adding a small amount of potassium hydroxide solution. Since the primary purpose of the ion exchange was to remove hydrogen cation (and metal cation) contaminates, this pH range is necessary to avoid redepositing hydrogen cation on the adsorbent mass. Washing temperatures can include temperatures within the range of about 35° C. to about 95° C. with a temperature of 55° C. to 65° C. preferred. Although the washing step can be done in a batch manner with one aliquot of wash water at a time, the washing step is generally and preferably done on a continuous flow type basis with water passed through a bed of the exchanged base material at a given liquid hourly space velocity and a temperature for a period of time in order that from about 1 to about 5 gallons of water per pound of starting material is used to wash the material. Preferred washing conditions include using liquid hourly space velocities from about 0.5 to about 5, with 1.5 being preferred, to pass from about 1 to about 3 gallons of wash water per pound of starting material over the ion exchanged adsorbent. A good indication of complete washing is made by measuring the pH of the effluent wash water and comparing it to the pH of the fresh feed wash water. When they are the same, washing can generally be considered as complete.

When the wash step is completed the wet adsorbent particles will usually contain from about 30 to about 50 wt. % volation matter (water) as measured by loss on ignition (L.O.I.) at 900° C. The remaining step in the method of manufacture then is the drying step in which the volatile content of the washed adsorbent is reduced to less than about 10 wt. % L.O.I. at 900° C. with the preferred volatile content being about 5 to 7 wt. % L.O.I. at 900° C. Drying conditions include the presence of air and can include temperature from about 35° C. to about 535° C. The time required to achieve the desired volatile content will vary depending upon the drying temperature and the exact volatile content of the water-washed adsorbent particles to be dried.

EXAMPLE

The following example is presented to illustrate the present invention and is not intended to unduly restrict the scope and spirit of the claims attached hereto.

This example presents pulse test results obtained with primarily two adsorbents, one containing potassium-type X zeolite and the other containing sodium-type X zeolite, each with several different desorbent materials. The pulse test results illustrate the ability of these two adsorbents to separate 1,3-butadiene from other $C_4$ unsaturates and the effect of desorbent material on adsorbent performance.

The adsorbents were prepared from Linde Molecular Sieves 13X base material which was in the form of a nominal 1/16-inch extrudate and which had a $Na_2O/Al_2O_3$ ratio of 0.61. This base material was ground to produce 20–40 U.S. Standard Mesh particle size material and this ground base material was then ion-exchanged with a dilute aqueous caustic solution (about 4 wt. % NaOH) for the purpose of eliminating polymerization activity of the final adsorbent. The sodium-exchanged base material had a $Na_2O/Al_2O_3$ ratio of 0.81. One portion of the sodium-exchanged base material was then water washed and dried to a water content of 1.4 wt. % L.O.I. at 900° C. to produce the adsorbent containing sodium-type X zeolite. Another portion of the sodium-exchanged base material was then ion-exchanged with a potassium chloride solution to give a volatile-free potassium oxide content of about 9 wt. %. The potassium-material was then water washed and dried to a water level of 1.5 wt. % L.O.I. at 900° C. to produce the adsorbent containing potassium-type X zeolite.

The pulse tests were performed in a 70 cc. adsorbent column which was maintained at constant temperature of 50° C. and at constant pressure to ensure liquid-phase operation during the entire test procedure. The column effluent was sampled every 2.5 minutes by an automatic sampling chromatograph. The feed mixture utilized comprised 20 vol. % each of butene-1, cis-butene-2, trans-butene-2, isobutylene, and 1,3-butadiene, to which was added a small amount of n-butane as a "tracer" for reference purposes. The mixture was injected into the test column in pulses of 3.6 cc. each. Different desorbent materials containing benzene or toluene in various concentrations were employed for the various pulse tests. The effluent was analyzed by the on-stream chromatograhic equipment and traces of the envelopes of component peaks were developed. From information derived from the chromatographic traces retention volumes and selectivities of the adsorbent were obtained. Additionally the widths of the butadiene peak envelopes, at half intensity, were measured as an indication of the rate of exchange of butadiene with different desorbent materials.

Results obtained for twelve pulse tests are shown in Table 2 below. Pulse tests 1 through 6 used the adsorbent containing potassium-type X zeolite while tests 7 through 12 used the adsorbent containing sodium-type X zeolite.

rior to one containing toluene when an adsorbent containing sodium-type X zeolite is used. The retention volumes and selectivities for tests 10–12 which used desorbent materials containing toluene were generally lower than those for tests 7–9 which used desorbent materials containing benzene. Comparing the results from tests 1–3 and 4–6 on the other hand indicates that with an adsorbent containing potassium-type X zeolite either a benzene-containing or a toluene-containing desorbent material can be employed.

I claim as my invention:

1. A process for separating 1,3-butadiene from a feed mixture comprising 1,3-butadiene and at least one $C_4$ mono-olefin which process comprises the steps of:
   a. contacting said mixture at adsorption conditions including the liquid phase with an adsorbent comprising type X zeolite containing potassium or sodium cations at the exchangeable cationic sites thereby selectively adsorbing 1,3-butadiene;
   b. withdrawing from the adsorbent a raffinate stream comprising a less selectively adsorbed $C_4$ mono-olefin;
   c. contacting the adsorbent at desorption conditions which include the liquid phase with a desorbent material comprising an aromatic hydrocarbon to effect the removal of 1,3-butadiene from the adsorbent;
   d. withdrawing from the adsorbent an extract stream comprising desorbent material and 1,3-butadiene and passing said extract stream to a separation means; and
   e. separating in said separation means, maintained at separating conditions, said desorbent material from 1,3-butadiene.

2. The process of claim 1 further characterized in that said mono-olefin is selected from the group consisting of isobutylene, 1-butene, trans-1-butene, cis-2-

Table 2

| Pulse Test | Adsorbent Zeolite Type | Desorbent Material | Pulse Test Data Summary Retention Volumes, ml | | | Butadiene Peak Half Width, ml | Selectivity, (B) | |
|---|---|---|---|---|---|---|---|---|
| | | | Butene 1 | 2 | Butadiene | | Butadiene Butene-2 | Butadiene Butene-1 |
| 1 | K-X | 75/25, Bz/n-C₇ | 2.3 | 4.6 | 20.2 | 15 | 8.8 | 4.4 |
| 2 | " | 50/50, Bz/n-C₇ | 2.1 | 4.2 | 24.0 | 16 | 11.4 | 5.7 |
| 3 | " | 100, Bz | 1.8 | 3.1 | 16.6 | 14(Tailing) | 9.2 | 5.4 |
| 4 | " | 100, Tol | 2.2 | 3.3 | 16.2 | 14(Tailing) | 7.4 | 4.9 |
| 5 | " | 75/25, Tol/n-C₇ | 1.3 | 3.3 | 17.3 | 14 | 13.3 | 5.2 |
| 6 | " | 50/50, Tol/n-C₇ | 1.5 | 3.4 | 22.7 | 16 | 15.1 | 6.7 |
| 7 | Na-X | 75/25, Bz/n-C₇ | 2.5 | 3.4 | 17.3 | 15 | 6.9 | 5.1 |
| 8 | " | 50/50, Bz/n-C₇ | 2.7 | 3.8 | 21.0 | 15 | 7.8 | 5.5 |
| 9 | " | 100, Bz | 2.1 | 4.0 | 14.7 | 15(Tailing) | 7.0 | 3.7 |
| 10 | " | 100, Tol | 1.4 | 1.8 | 6.8 | 13(Tailing) | 4.8 | 3.8 |
| 11 | " | 75/25, Tol/n-C₇ | 1.7 | 2.4 | 8.0 | 13 | 4.7 | 3.3 |
| 12 | " | 50/50, Tol/n-C₇ | 1.3 | 2.0 | 10.0 | 14 | 7.7 | 5.0 |

The selectivity values shown for the twelve pulse tests demonstrate first of all the ability of both adsorbents to selectively adsorb 1,3-butadiene from a feed stream containing 1,3-butadiene and at least one other $C_4$ unsaturate, thereby making possible the butadiene separation process of this invention. All selectivities were at least about 3 or greater. The data for pulse tests 3 and 4 and 9 and 10 indicate that tailing rather than clean desorption of 1,3-butadiene occurred when either 100 vol. % benzene or toluene was used as the desorbent material. Although selectivities did not suffer to any degree, tailing could effect the yield or purity of butadiene recovered from a continuous separation process. The data for tests 7–9 and 10–12 also indicates that a desorbent material containing benzene is superior to one containing toluene when an adsorbent containing butene, and 3-methyl-1-butene.

3. The process of claim 1 further characterized in that said adsorption and desorption conditions include temperatures within the range of from about 25° C. to about 75° C. and pressures from about atmospheric to about 500 psig.

4. The process of claim 1 further characterized in that the adsorbent comprises sodium-type X zeolite.

5. The process of claim 4 further characterized in that said adsorbent is produced by the steps of:
   a. contacting a base material comprising a type X zeolite having a $Na_2O/Al_2O_3$ ratio less than about 0.7 with an aqueous sodium hydroxide solution at ion exchange conditions to increase the sodium cation content to a $Na_2O/Al_2O_3$ ratio of greater than about 0.7;
b. washing the material with water maintained at pH greater than 7 to remove excess sodium hydroxide solution; and
c. drying the material at drying conditions to reduce the LOI at 900° C. to less than about 10 wt. %.

6. The process of claim 5 further characterized in that said base material comprises Linde Molecular Sieve 13X.

7. The process of claim 4 further characterized in that the desorbent material comprises benzene.

8. The process of claim 1 further characterized in that the adsorbent comprises potassium-type X zeolite.

9. The process of claim 8 further characterized in that said adsorbent is produced by the steps of:
 a. contacting a base material comprising a type X zeolite having a $Na_2O/Al_2O_3$ ratio less than about 0.7 with an aqueous sodium hydroxide solution at first ion exchange conditions to increase the sodium cation content to a $Na_2O/Al_2O_3$ ratio of greater than about 0.7;
 b. contacting the sodium-exchanged base material with an aqueous potassium salt solution at second ion exchange conditions to effect the essentially complete exchange of sodium cations with potassium cations;
 c. washing the material with water maintained at pH greater than 7 to remove excess potassium salt solution; and
 d. drying the material at drying conditions to reduce the LOI, at 900° C. to less than about 10 wt. %.

10. The process of claim 9 further characterized in that said base material comprises Linde Molecular Sieves 13X.

11. The process of claim 8 further characterized in that said desorbent material comprises benzene or toluene.

12. A process for separating 1,3-butadiene from a feed mixture comprising 1,3-butadiene and at least one $C_4$ mono-olefin which comprises the steps of:
 a. contacting said mixture at adsorption conditions including the liquid phase with an adsorbent prepared by the steps of:
  i. contacting a base material comprising type X zeolite having a $Na_2O/Al_2O_3$ ratio less than about 0.7 with an aqueous sodium hydroxide solution at first ion exchange conditions to increase the sodium cation content to a $Na_2O/Al_2O_3$ ratio of greater than about 0.7;
  ii. contacting the sodium-exchanged base material with an aqueous potassium salt solution at second ion exchange conditions to effect the essentially complete exchange of sodium cations with potassium cations;
  iii. washing the material with water maintained at pH greater than 7 to remove excess potassium salt solution; and
  iv. drying the material at drying conditions to reduce the LOI at 900° C. to less than about 10 wt. %; thereby selectively adsorbing 1,3-butadiene;
 b. withdrawing from the adsorbent a raffinate stream comprising a less selectively adsorbed $C_4$ mono-olefin;
 c. contacting the adsorbent at desorption conditions which include the liquid phase with a desorbent material comprising benzene or toluene to effect the removal of 1,3-butadiene from the adsorbent;
 d. withdrawing from the adsorbent an extract stream comprising 1,3-butadiene and desorbent material and passing said extract stream to a fractionation means; and
 e. fractionating in said fractionation means maintained at fractionation conditions desorbent material from 1,3-butadiene.

13. The process of claim 12 further characterized in that said adsorption and desorption conditions include temperatures within the range of from about 25° C. to about 75° C. and pressures from about atmospheric to about 500 psig.

14. The process of claim 12 further characterized in that said base material comprises Linde Molecular Sieves 13X.

15. The process of claim 12 further characterized in that said desorbent material comprises a mixture of benzene or toluene and a paraffin or a naphthene.

* * * * *